US009649061B2

(12) United States Patent
Ivosevic et al.

(10) Patent No.: US 9,649,061 B2
(45) Date of Patent: May 16, 2017

(54) BIOLOGICAL FLUID MICRO-SAMPLE MANAGEMENT DEVICE

(71) Applicant: Becton, Dickinson and Company, Franklin Lakes, NJ (US)

(72) Inventors: Milan Ivosevic, Kinnelon, NJ (US); Kishore K. Bokka Srinivasa Rao, Ridgewood, NJ (US); Peter Skutnik, Midland Park, NJ (US); Anthony V. Torris, Montclair, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/065,022

(22) Filed: Mar. 9, 2016

(65) Prior Publication Data
US 2016/0262679 A1 Sep. 15, 2016

Related U.S. Application Data

(60) Provisional application No. 62/130,878, filed on Mar. 10, 2015.

(51) Int. Cl.
*B01L 3/00* (2006.01)
*A61B 5/15* (2006.01)
(Continued)

(52) U.S. Cl.
CPC ........ *A61B 5/150755* (2013.01); *B01L 3/502* (2013.01); *A61B 5/154* (2013.01);
(Continued)

(58) Field of Classification Search
CPC .............................. B01L 3/5082; B01L 3/5453
(Continued)

(56) References Cited

U.S. PATENT DOCUMENTS 3,819,913 A 6/1974 Carter et al.
3,916,205 A 10/1975 Kleinerman
(Continued)

FOREIGN PATENT DOCUMENTS

EP 0545500 A1 6/1993
EP 0663070 B1 7/1995
(Continued)

*Primary Examiner* — Natalia Levkovich
(74) *Attorney, Agent, or Firm* — The Webb Law Firm

(57) ABSTRACT

A biological fluid collection device includes a collection module and an outer housing. The collection module includes a housing comprising a first end having a sample introduction opening, a second end having a sample dispensing opening, and a passageway extending between the sample introduction opening and the sample dispensing opening. A mixing chamber and a holding chamber are in fluid communication with the passageway such that a sample introduced into the sample introduction opening passes through the mixing chamber and subsequently into the holding chamber. The biological fluid collection device further includes a closure covering the first end, a cap covering the second end and including a vented plug, and an activation member adapted to force a sample contained in the holding chamber out of the sample dispensing opening. The collection module is positioned inside of the outer housing and the closure closes the open end of the outer housing.

8 Claims, 7 Drawing Sheets

(51) Int. Cl.
　　　*B01L 3/02*　　　　　(2006.01)
　　　*A61B 5/154*　　　　(2006.01)
(52) U.S. Cl.
　　　CPC ....... *A61B 5/150022* (2013.01); *B01L 3/0272* (2013.01); *B01L 3/0296* (2013.01); *B01L 2200/0605* (2013.01); *B01L 2300/021* (2013.01); *B01L 2300/048* (2013.01); *B01L 2300/0609* (2013.01); *B01L 2300/087* (2013.01); *B01L 2300/0832* (2013.01); *B01L 2300/0838* (2013.01); *B01L 2400/049* (2013.01); *B01L 2400/0475* (2013.01); *B01L 2400/0481* (2013.01)
(58) Field of Classification Search
　　　USPC .................................................. 422/549, 550
　　　See application file for complete search history.

(56) References Cited

U.S. PATENT DOCUMENTS

| | | |
|---|---|---|
| 3,963,350 A | 6/1976 | Watanabe et al. |
| 4,088,448 A | 5/1978 | Lilja et al. |
| 4,125,828 A | 11/1978 | Resnick et al. |
| 4,133,304 A | 1/1979 | Bailey |
| 4,133,873 A | 1/1979 | Noller |
| 4,337,222 A | 6/1982 | Kitajima et al. |
| 4,501,496 A | 2/1985 | Griffin |
| 4,703,761 A | 11/1987 | Rathbone et al. |
| 4,727,020 A | 2/1988 | Recktenwald |
| 4,751,188 A | 6/1988 | Valet |
| 4,857,735 A | 8/1989 | Noller |
| 4,959,305 A | 9/1990 | Woodrum |
| 5,014,718 A | 5/1991 | Mitchen |
| 5,053,626 A | 10/1991 | Tillotson |
| 5,073,857 A | 12/1991 | Peters et al. |
| 5,102,625 A | 4/1992 | Milo |
| 5,134,662 A | 7/1992 | Bacus et al. |
| 5,159,642 A | 10/1992 | Kosaka |
| 5,187,749 A | 2/1993 | Sugimoto et al. |
| 5,196,709 A | 3/1993 | Berndt et al. |
| 5,200,152 A | 4/1993 | Brown |
| 5,294,799 A | 3/1994 | Aslund et al. |
| 5,332,905 A | 7/1994 | Brooker et al. |
| 5,348,859 A | 9/1994 | Brunhouse et al. |
| 5,385,539 A | 1/1995 | Maynard |
| 5,489,771 A | 2/1996 | Beach et al. |
| 5,491,343 A | 2/1996 | Brooker |
| 5,528,045 A | 6/1996 | Hoffman et al. |
| 5,547,849 A | 8/1996 | Baer et al. |
| 5,556,764 A | 9/1996 | Sizto et al. |
| 5,592,291 A | 1/1997 | Iida |
| 5,599,668 A | 2/1997 | Stimpson et al. |
| 5,627,037 A | 5/1997 | Ward et al. |
| 5,661,558 A | 8/1997 | Nogami et al. |
| 5,674,457 A | 10/1997 | Williamsson et al. |
| 5,675,155 A | 10/1997 | Pentoney, Jr. et al. |
| 5,681,529 A | 10/1997 | Taguchi et al. |
| 5,692,503 A | 12/1997 | Kuenstner |
| 5,732,150 A | 3/1998 | Zhou et al. |
| 5,733,721 A | 3/1998 | Hemstreet, III et al. |
| 5,773,301 A | 6/1998 | Ziegler |
| 5,851,835 A | 12/1998 | Groner |
| 5,898,487 A | 4/1999 | Hage |
| 5,933,233 A | 8/1999 | Gunther |
| 5,938,439 A | 8/1999 | Mertins et al. |
| 6,043,880 A | 3/2000 | Andrews et al. |
| 6,064,474 A | 5/2000 | Lee et al. |
| 6,064,897 A | 5/2000 | Lindberg et al. |
| 6,094,592 A | 7/2000 | Yorkey et al. |
| 6,103,197 A | 8/2000 | Werner |
| 6,154,282 A | 11/2000 | Lilge et al. |
| 6,159,740 A | 12/2000 | Hudson et al. |
| 6,181,418 B1 | 1/2001 | Palumbo et al. |
| 6,187,592 B1 | 2/2001 | Gourley |
| 6,214,629 B1 | 4/2001 | Freitag et al. |
| 6,226,347 B1 | 5/2001 | Golenhofen |
| 6,262,798 B1 | 7/2001 | Shepherd et al. |
| 6,294,094 B1 | 9/2001 | Muller et al. |
| 6,305,804 B1 | 10/2001 | Rice et al. |
| 6,342,376 B1 | 1/2002 | Kozian et al. |
| 6,350,613 B1 | 2/2002 | Wardlaw et al. |
| 6,410,341 B1 | 6/2002 | Freitag et al. |
| 6,453,060 B1 | 9/2002 | Riley et al. |
| 6,477,394 B2 | 11/2002 | Rice et al. |
| 6,479,299 B1 | 11/2002 | Parce et al. |
| 6,493,567 B1 | 12/2002 | Krivitski et al. |
| 6,519,025 B2 | 2/2003 | Shepherd et al. |
| 6,563,585 B1 | 5/2003 | Rao et al. |
| 6,594,075 B1 | 7/2003 | Kanao et al. |
| 6,611,320 B1 | 8/2003 | Lindberg et al. |
| 6,612,111 B1 | 9/2003 | Hodges et al. |
| 6,638,769 B2 | 10/2003 | Lilja et al. |
| 6,665,060 B1 | 12/2003 | Zahniser et al. |
| 6,696,240 B1 | 2/2004 | Kloepfer et al. |
| 6,716,588 B2 | 4/2004 | Sammak et al. |
| 6,723,290 B1 | 4/2004 | Wardlaw |
| 6,740,527 B1 | 5/2004 | Wong et al. |
| 6,825,921 B1 | 11/2004 | Modlin et al. |
| 6,828,567 B2 | 12/2004 | Amirkhanian et al. |
| 6,831,733 B2 | 12/2004 | Pettersson et al. |
| 6,858,400 B2 | 2/2005 | Bristow |
| 6,862,534 B2 | 3/2005 | Sterling et al. |
| 6,869,570 B2 | 3/2005 | Wardlaw |
| 6,898,458 B2 | 5/2005 | Zeng et al. |
| 6,960,165 B2 | 11/2005 | Ueno et al. |
| 6,985,224 B2 | 1/2006 | Hart |
| 6,999,173 B2 | 2/2006 | Kleinfeld et al. |
| 7,075,628 B2 | 7/2006 | Shepherd et al. |
| 7,094,562 B2 | 8/2006 | Bittner |
| 7,096,124 B2 | 8/2006 | Sterling et al. |
| 7,115,841 B2 | 10/2006 | Zeng et al. |
| 7,133,545 B2 | 11/2006 | Douglass et al. |
| 7,146,372 B2 | 12/2006 | Bacus et al. |
| 7,149,332 B2 | 12/2006 | Bacus et al. |
| 7,271,912 B2 | 9/2007 | Sterling et al. |
| 7,279,134 B2 | 10/2007 | Chan et al. |
| 7,303,922 B2 | 12/2007 | Jeng et al. |
| 7,319,894 B2 | 1/2008 | Higgins |
| 7,324,674 B2 | 1/2008 | Ozawa et al. |
| 7,420,660 B2 | 9/2008 | Muller |
| 7,426,407 B2 | 9/2008 | Higgins |
| 7,477,382 B2 | 1/2009 | Grey et al. |
| 7,515,268 B1 | 4/2009 | Ayliffe et al. |
| 7,518,727 B2 | 4/2009 | Pentoney, Jr. et al. |
| 7,539,335 B2 | 5/2009 | Fukuyama |
| 7,560,073 B1 | 7/2009 | Peters et al. |
| 7,625,712 B2 | 12/2009 | Paul et al. |
| 7,630,063 B2 | 12/2009 | Padmanabhan et al. |
| 7,674,598 B2 | 3/2010 | Paul et al. |
| 7,738,094 B2 | 6/2010 | Goldberg |
| 7,762,946 B2 | 7/2010 | Sugimoto |
| 7,781,226 B2 | 8/2010 | McDevitt et al. |
| 7,790,464 B2 | 9/2010 | Tarasev |
| 7,816,135 B2 | 10/2010 | Goldberg |
| 7,826,728 B2 | 11/2010 | Konno et al. |
| 7,854,891 B2 | 12/2010 | Yamamoto et al. |
| 7,892,551 B2 | 2/2011 | Glencross |
| 7,903,241 B2 | 3/2011 | Wardlaw et al. |
| 7,952,692 B2 | 5/2011 | Primack et al. |
| 8,009,894 B2 | 8/2011 | Lindberg et al. |
| 8,125,623 B2 | 2/2012 | Munger et al. |
| 8,224,058 B2 | 7/2012 | Lindberg et al. |
| 8,244,021 B2 | 8/2012 | Lett et al. |
| 8,306,594 B2 | 11/2012 | Paseman et al. |
| 8,353,848 B2 | 1/2013 | Long et al. |
| 8,377,398 B2 | 2/2013 | McDevitt et al. |
| 8,406,859 B2 | 3/2013 | Zuzak et al. |
| 8,483,789 B2 | 7/2013 | Higgins |
| 8,488,903 B2 | 7/2013 | Higuchi |
| 8,541,227 B2 | 9/2013 | Christensen et al. |
| 2003/0152927 A1 | 8/2003 | Jakobsen et al. |
| 2003/0170613 A1 | 9/2003 | Straus |
| 2003/0206828 A1 | 11/2003 | Bell |

(56) References Cited

U.S. PATENT DOCUMENTS

| | | |
|---|---|---|
| 2003/0230728 A1 | 12/2003 | Dai et al. |
| 2004/0224329 A1 | 11/2004 | Gjerde et al. |
| 2005/0054949 A1 | 3/2005 | McKinnon et al. |
| 2005/0142565 A1 | 6/2005 | Samper et al. |
| 2005/0190058 A1 | 9/2005 | Call |
| 2006/0024756 A1 | 2/2006 | Tibbe et al. |
| 2006/0060531 A1 | 3/2006 | Coville et al. |
| 2006/0241495 A1 | 10/2006 | Kurtz |
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2008/0190220 A1 | 8/2008 | Backes et al. |
| 2008/0203319 A1 | 8/2008 | Pentoney et al. |
| 2008/0268469 A1 | 10/2008 | Srienc et al. |
| 2009/0075324 A1 | 3/2009 | Pettersson |
| 2009/0107903 A1 | 4/2009 | Dassa |
| 2009/0181411 A1 | 7/2009 | Battrell et al. |
| 2009/0259145 A1* | 10/2009 | Bartfeld ............... A61B 5/1405 600/576 |
| 2010/0291599 A1 | 11/2010 | Tague, Jr. et al. |
| 2011/0118139 A1 | 5/2011 | Mehta et al. |
| 2011/0159457 A1 | 6/2011 | Offermann |
| 2012/0016307 A1 | 1/2012 | Burkholz et al. |
| 2012/0123297 A1 | 5/2012 | Brancazio |
| 2013/0045529 A1 | 2/2013 | Goldberg et al. |
| 2013/0162990 A1 | 6/2013 | Kobayashi et al. |
| 2014/0093896 A1 | 4/2014 | Mongale et al. |
| 2014/0200154 A1 | 7/2014 | Sugarman et al. |
| 2015/0125882 A1 | 5/2015 | Bornheimer et al. |
| 2015/0132789 A1 | 5/2015 | Bornheimer et al. |

FOREIGN PATENT DOCUMENTS

| | | |
|---|---|---|
| EP | 0681177 A1 | 11/1995 |
| EP | 0737855 A1 | 10/1996 |
| EP | 0744600 A1 | 11/1996 |
| EP | 0788615 B1 | 8/1997 |
| EP | 0800074 A1 | 10/1997 |
| EP | 0818682 A2 | 1/1998 |
| EP | 0821784 B1 | 11/1998 |
| EP | 0959346 A2 | 11/1999 |
| EP | 0969279 A2 | 1/2000 |
| EP | 0809807 B1 | 7/2002 |
| EP | 1324021 A1 | 7/2003 |
| EP | 1347702 A2 | 10/2003 |
| EP | 1456649 B1 | 6/2006 |
| EP | 1698883 A1 | 9/2006 |
| EP | 1701150 A1 | 9/2006 |
| EP | 1767935 A1 | 3/2007 |
| EP | 1924195 A2 | 5/2008 |
| EP | 1990638 A1 | 11/2008 |
| EP | 2016390 A1 | 1/2009 |
| EP | 2041549 A1 | 4/2009 |
| EP | 2083687 A1 | 8/2009 |
| EP | 1405073 B1 | 3/2010 |
| EP | 2232442 A1 | 9/2010 |
| EP | 2016390 B1 | 4/2013 |
| EP | 2586370 A2 | 5/2013 |
| EP | 2605020 A2 | 6/2013 |
| EP | 1558934 B1 | 7/2013 |
| EP | 2676606 A1 | 12/2013 |
| JP | 200188098 A | 4/2001 |
| JP | 2002506208 A | 2/2002 |
| JP | 2002516982 A | 6/2002 |
| JP | 2008525768 A | 7/2008 |
| WO | 9920998 A1 | 4/1999 |
| WO | 9945384 A1 | 9/1999 |
| WO | 0028297 A2 | 5/2000 |
| WO | 0029847 A2 | 5/2000 |
| WO | 0244729 A1 | 6/2002 |
| WO | 0250518 A2 | 6/2002 |
| WO | 03036290 A1 | 5/2003 |
| WO | 2004100887 A2 | 11/2004 |
| WO | 2005100539 A2 | 10/2005 |
| WO | 2006047831 A1 | 5/2006 |
| WO | 2006096126 A1 | 9/2006 |
| WO | 2006119368 A2 | 11/2006 |
| WO | 2007012975 A1 | 2/2007 |
| WO | 2007033318 A2 | 3/2007 |
| WO | 2007051861 A1 | 5/2007 |
| WO | 2007111555 A1 | 10/2007 |
| WO | 2007129948 A1 | 11/2007 |
| WO | 2008002462 A2 | 1/2008 |
| WO | 2008010761 A1 | 1/2008 |
| WO | 2008037068 A1 | 4/2008 |
| WO | 2008103992 A2 | 8/2008 |
| WO | 2009091318 A1 | 7/2009 |
| WO | 2009155612 A3 | 12/2009 |
| WO | 2010003518 A1 | 1/2010 |
| WO | 2010085658 A1 | 7/2010 |
| WO | 2011133540 A2 | 10/2011 |
| WO | 2013075031 A1 | 5/2013 |

* cited by examiner

BIOLOGICAL FLUID MICRO-SAMPLE MANAGEMENT DEVICE

CROSS REFERENCE TO RELATED APPLICATIONS

This application claims benefit of U.S. Provisional Patent Application No. 62/130,878 entitled "Biological Fluid Micro-Sample Management Device" filed Mar. 10, 2015, which is hereby incorporated by reference in its entirety.

BACKGROUND OF THE INVENTION

Field of the Invention

The present invention is directed to a biological fluid collection device, specifically a blood collection device for collecting a small sample of blood and dispensing a portion of the sample into a device intended or designed to analyze the sample such as point-of-care or a near-patient-testing device.

Description of Related Art

A need exists for an improved device which enables collection of a micro-sample, such as less than 500 microliters of collected sample for analysis, such as patient point-of-care applications. Current devices require conventional sample collection and the subsequent use of a 1 ml syringe or pipette to transfer a small blood sample to a point-of-care cartridge or instrument receiving port. This open system approach results in an increased blood exposure risk for personnel performing the testing, as well as the collection of excess specimen required for a specified test procedure.

It is therefore desirable to have a blood sample collection and dispensing tool for point-of-care applications which incorporates conventional automatic blood draw and includes a novel controlled sample dispensing capability while minimizing exposure risk.

SUMMARY OF THE INVENTION

The present invention is directed to a biological fluid collection device including a collection module and an outer housing. The collection module includes a housing having a first end having a sample introduction opening, a second end having a sample dispensing opening, and a passageway extending between the sample introduction opening and the sample dispensing opening. A mixing chamber and a holding chamber are in fluid communication with the passageway such that a sample introduced into the sample introduction opening passes through the mixing chamber and subsequently into the holding chamber. The collection module further includes a closure covering the first end of the housing, a cap covering the second end of the housing and having a vented plug, and an activation member adapted to force a sample contained in the holding chamber out of the sample dispensing opening. The collection module is positioned inside of the outer housing and the closure of the collection module closes the open end of the outer housing.

The mixing chamber may include an anticoagulant disposed therein. The mixing chamber may also include an open cell foam.

The cap may include a vented plug, such as a porous plug, that allows air to pass therethrough and prevents a blood sample from passing therethrough. The vented plug may stop the flow of the blood sample into the collection device when the passageway of the housing is filled with blood.

The mixing chamber may be positioned closer to the first end of the housing than the holding chamber such that a blood sample introduced into the sample introduction opening passes through the mixing chamber before passing into the holding chamber.

The holding chamber may be defined by an elastic sleeve surrounding a portion of the housing and a recess in the housing, and the activation member may be at least a portion of the elastic sleeve defining the holding chamber. When the cap is removed from the collection device and an inward pressure is placed on the portion of the elastic sleeve defining the holding chamber in a direction toward the recess in the housing, the blood sample in the holding chamber may be forced out of the sample dispensing opening.

DESCRIPTION OF THE INVENTION

Figure 2:
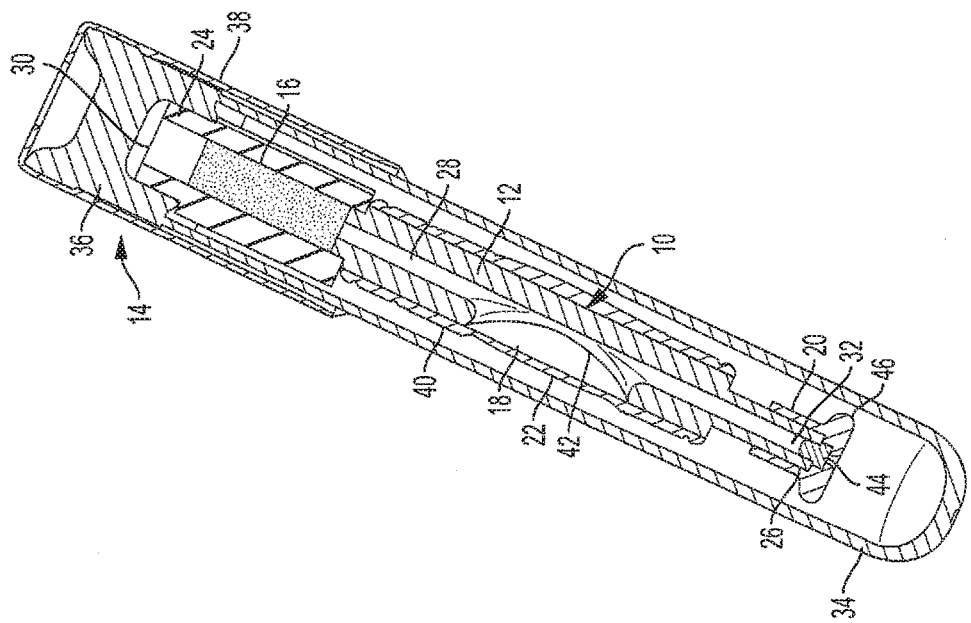
FIG. 2 is a partial cross-sectional perspective view of the biological fluid collection device of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
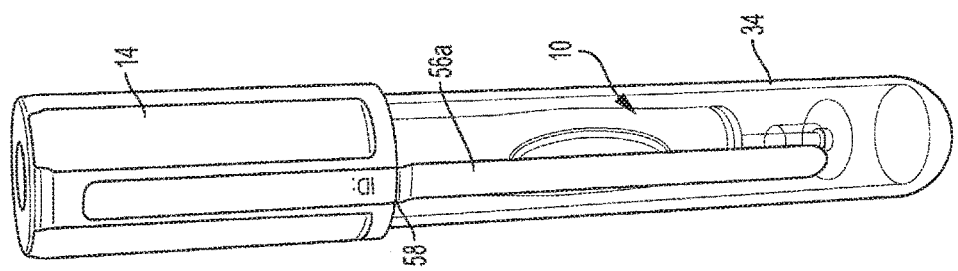
FIG. 1 is a front perspective view of a biological fluid collection device having a collection module disposed within an outer housing in accordance with an aspect of the present invention.

Referring to FIGS. 1 and 2, a biological fluid collection device includes a collection module 10 disposed within an outer housing 34. The collection module 10 is adapted to receive a biological fluid sample, such as a blood sample, and includes a housing 12, a closure 14, a mixing chamber 16, a holding chamber 18, a cap 20, and an activation member 22.

In one embodiment, the housing 12 includes a first end 24, a second end 26, and a passageway 28 extending therebetween and providing fluid communication between the first end 24 and the second end 26 of the housing 12. The passageway 28 has a sample introduction opening 30 at the first end 24 of the housing 12 and a sample dispensing opening 32 at the second end 26 of the housing 12. The mixing chamber 16 and the holding chamber 18 are provided in fluid communication with the passageway 28. The mixing chamber 16 and the holding chamber 18 are positioned such that a biological fluid sample, such as a blood sample, introduced into the sample introduction opening 30 of the passageway 28 will first pass through the mixing chamber 16 and subsequently pass into the holding chamber 18, prior to reaching the sample dispensing opening 32 of the passageway 28. In this way, the blood sample may be mixed with an anticoagulant or other additive provided within the mixing chamber 16 before the stabilized sample is received and stored within the holding chamber 18.

The mixing chamber 16 allows for passive mixing of the blood sample with an anticoagulant or another additive, such as a blood stabilizer, as the blood sample flows through the passageway 28. The internal portion of the mixing chamber 16 may have any suitable structure or form as long as it provides for the mixing of the blood sample with an anticoagulant or another additive as the blood sample passes through the passageway 28. The mixing chamber 16 may include a dry anticoagulant, such as Heparin or EDTA, deposited on or within the mixing chamber 16. The mixing chamber 16 may, for example, include an open cell foam (FIG. 1) containing dry anticoagulant dispersed within the cells of the open cell foam to promote the effectiveness of the flow-through mixing and anticoagulant uptake.

The open cell foam may be treated with an anticoagulant to form a dry anticoagulant powder finely distributed throughout the pores of the open cell foam. As the blood sample enters the mixing chamber 16, the blood sample passes through the open cell foam and is exposed to the anticoagulant powder available throughout the internal pore structure of the open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

After passing through the mixing chamber 16, the blood sample may be directed to the holding chamber 18. The holding chamber 18 may take any suitable shape and size to store a sufficient volume of blood necessary for the desired testing, for example 500 µl or less. In the embodiment shown in FIGS. 1 and 2, the holding chamber 18 is defined by a portion of the housing 12 in combination with an elastic sleeve 40 secured about the exterior of the housing 12. The elastic sleeve 40 may be made of any material that is flexible, deformable, and capable of providing a fluid tight seal with the housing 12, including, but not limited to, natural or synthetic rubber, and other suitable elastomeric materials. The housing 12 includes a recess 42 that extends from the exterior of the housing 12 to the passageway 28 effectively creating an opening in the housing 12 in fluid communication with the passageway 28. The elastic sleeve 40 covers the recess 42 defining the holding chamber 18 having an internal fill volume of 500 µl or less.

A cap 20 disposed at the second end 26 of the housing 12 covers the sample dispensing opening 32 of the passageway 28. The cap 20 includes a vented plug, such as a porous plug 44, extending from the interior surface of the cap 20 to the exterior surface of the cap 20. The construction of the vented plug 44 allows air to pass through the cap 20 while preventing the blood sample from passing through the cap 20 and may include a hydrophobic filter. The vented plug 44 has selected air passing resistance that may be used to finely control the filling rate of the passageway 28. By varying the porosity of the plug, the velocity of the air flow out of the cap 20, and thus the velocity of the blood sample flow into the collection module 10, may be controlled. If the blood sample flow velocity into the collection module 10 is too fast, hemolysis may occur. If the blood sample flow velocity into the collection module 10 is too slow, sample collection time may be excessive.

A closure 14 is engaged with the first end 24 of the housing 12 to seal the passageway 28. The closure 14 allows for introduction of a blood sample into the passageway 28 of the housing 12 and may include a pierceable self-sealing stopper 36 with an outer shield 38 such as a Hemogard™ cap commercially available from Becton, Dickinson and Company. The closure 14 also secures to the outer housing 34 which may be a vacuum containing blood collection tube such as a Vacutainer® blood collection tube commercially available from Becton, Dickinson and Company.

Figure 7:
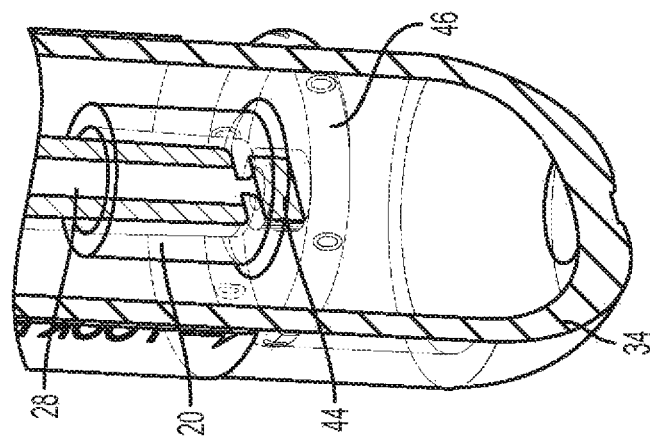
FIG. 7 is a partial cross-sectional perspective view of the lower end of the biological fluid collection device of FIG. 6.
Figure 6:
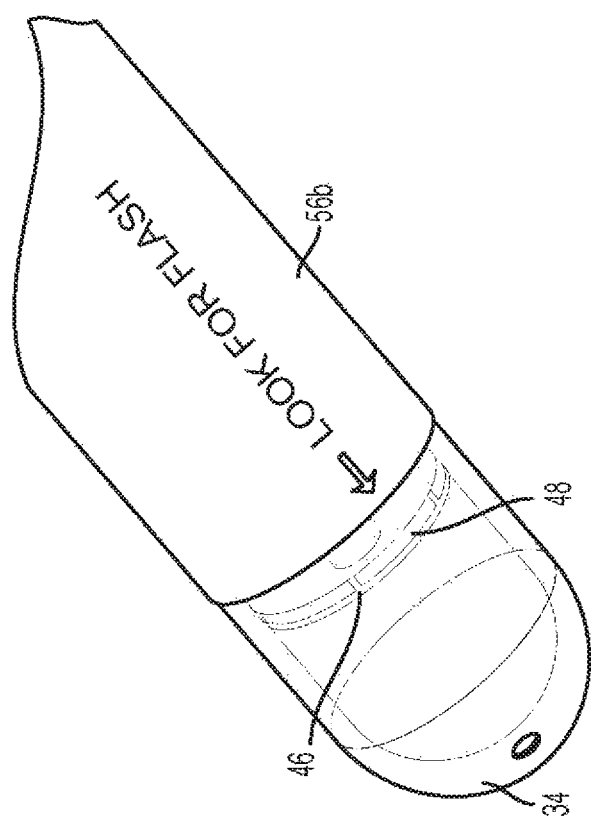
FIG. 6 is a partial perspective view of the lower end of a biological fluid collection device having a biological fluid collection module disposed within an outer collection housing in accordance with another aspect of the present invention.

The cap 20 disposed at the second end 26 of the housing 12 may also include a flange 46 to assist the user in removing the cap 20 from the housing 12. As shown in FIG. 2, the flange may have an outer diameter that is less than the inner diameter of the outer housing 34 in which the collection module 10 may be placed. Alternatively, as shown in FIGS. 6 and 7, the flange 46 may have an outer diameter substantially equal to the inner diameter of the outer housing 34. In this configuration, the flange 46 may include recesses or slots 48 extending from an upper surface to a lower surface to allow a vacuum within the outer housing 34 to pass around the flange 46. In addition, as shown in FIGS. 6 and 7, the flange 46 may be made of an optically clear material and may have a convex outer diameter surface such that it magnifies the vented plug 44 area of the cap 20 allowing a medical practitioner to see when the blood sample has fully filled the passageway 28 and reached the cap 20. The flange 46 may also be engaged with a recess of the interior wall of the outer housing 34 to restrain the cap 20 therewith.

In use, a needle cannula 50 (FIGS. 5A and 5C) is inserted into the passageway 28 of the housing 12 through the sample introduction opening 30, such as through the pierceable self-sealing stopper 36 of closure 14. As shown in FIG. 5A, the combined collection module 10 and the outer housing 34 may be inserted into a conventional tube holder 52 having a cannula through which biological fluid is passed.

Figure 5B:
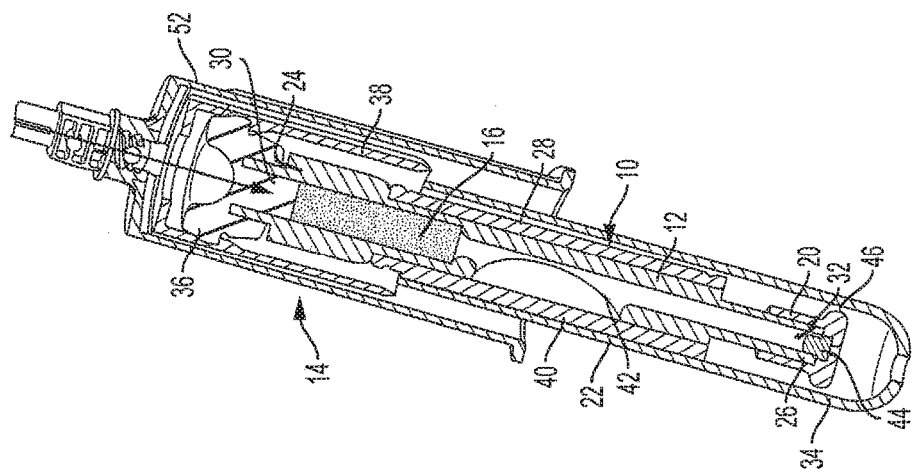
FIG. 5B is a partial cross-sectional perspective view of the biological fluid collection device of FIG. 1 wherein a biological fluid sample is flowing into the collection module through a tube holder.
Figure 5A:
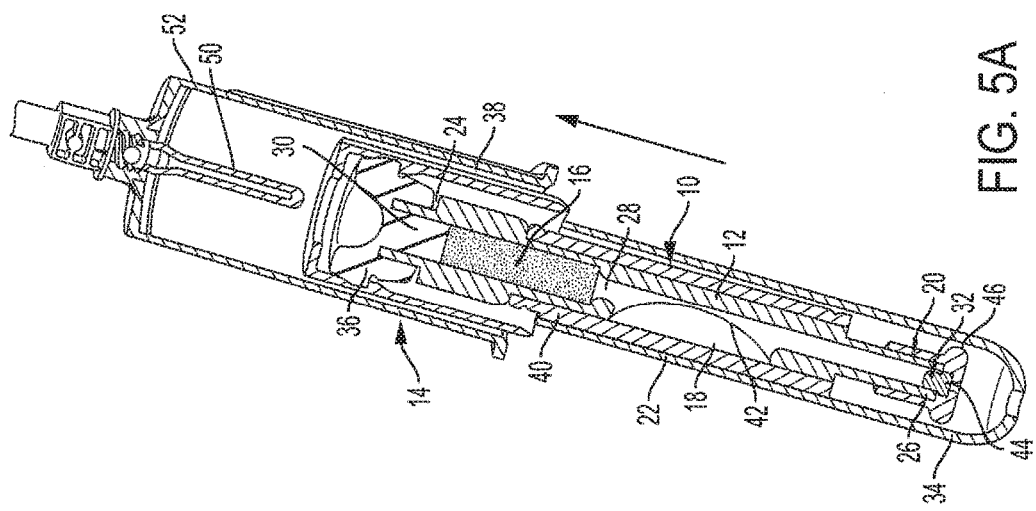
FIG. 5A is a partial cross-sectional perspective view of the biological fluid collection device of FIG. 1 being inserted into a tube holder in accordance with an aspect of the present invention.

The biological fluid sample is pulled into the passageway 28 of the housing 12 from the conventional tube holder 52 by the draw of the vacuum contained in the outer housing 34 (FIG. 5B). The blood sample fills the entire passageway 28 by first entering the mixing chamber 16 and subsequently the holding chamber 18 and expels any air present in the passageway 28 into the outer housing 34. As described above, the biological fluid sample is exposed to, and mixed with, an anticoagulant or other additive as it passes through the mixing chamber 16. The cap 20 stops the collection of the blood sample when the passageway 28, mixing chamber 16, and holding chamber 18 of the collection module 10 has been fully filled. The vented plug 44 of the cap 20 prevents blood from passing into the outer housing 34.

Figure 5D:
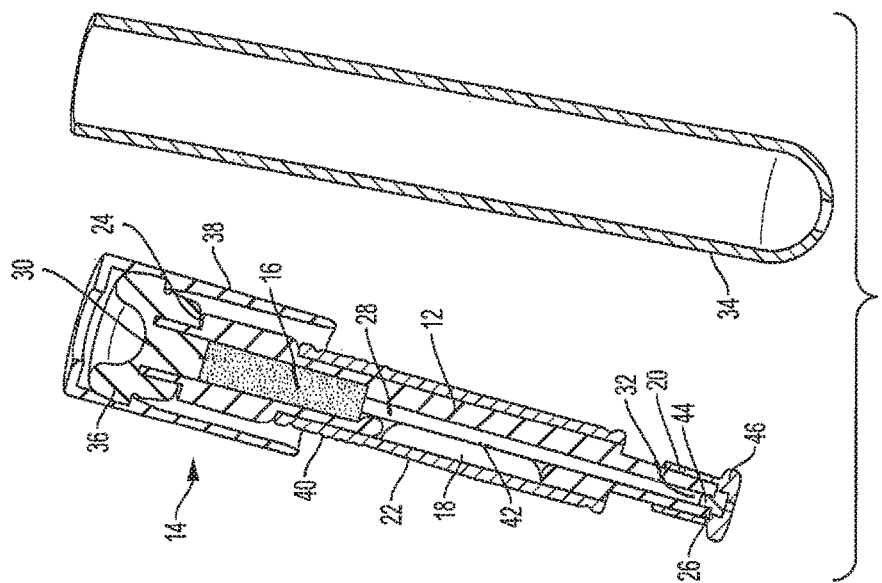
FIG. 5D is a partial cross-sectional perspective view of the collection module of the biological fluid collection device of FIG. 1 removed from the outer housing of FIG. 1 in accordance with an aspect of the present invention.
Figure 5C:
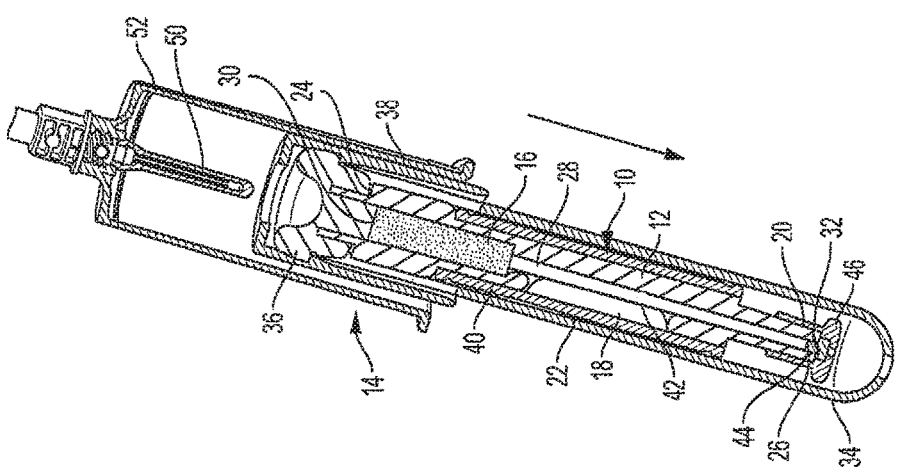
FIG. 5C is a partial cross-sectional perspective view of the biological fluid collection device of FIG. 1 being removed from a tube holder in accordance with an aspect of the present invention.

Once sample collection is complete, the outer housing 34 including the collection module 10 is separated from the tube holder 52 (FIG. 5C), and then the outer housing 34 is separated from the collection module 10 (FIG. 5D) by removing the closure 14, which is still attached to the collection module 10, from the outer housing 34. Removal of the closure 14 may be accomplished by the user grasping both the outer shield 38 of the closure 14 and the outer housing 34 and pulling or twisting them in opposite directions.

Figure 5E:
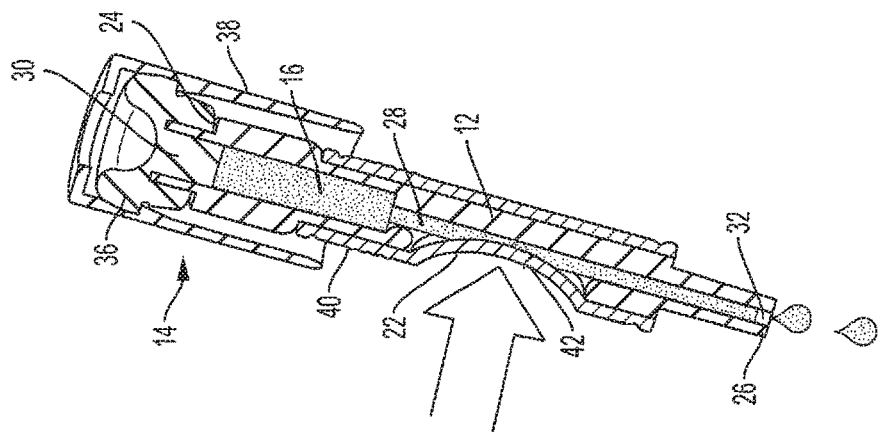
FIG. 5E is a partial cross-sectional perspective view of the cap being removed from the collection module of the biological fluid collection device of FIG. 1 in accordance with an aspect of the present invention.

Once the collection module 10 is separated from the outer housing 34, the cap 20 may then be removed from the collection module 10 (FIG. 5E) exposing the second end 26 of the housing 12. Removal may be accomplished by the user grasping the flange 46 and pulling the cap 20 from the housing 12. The blood sample is held within the passageway 28 of the housing 12 by capillary action after removal of the cap 20. Alternatively, removal of the cap 20 may occur upon removal of the collection module 10 from the outer housing 34. In this configuration, the cap 20 is restrained within the outer housing 34 by the interaction of the flange 46 and corresponding recess of the outer housing wall. In a further embodiment, the cap 20 may be connected to the outer housing 34 so that the outer housing 34 and the cap 20 are removed in one step.

Figure 5F:
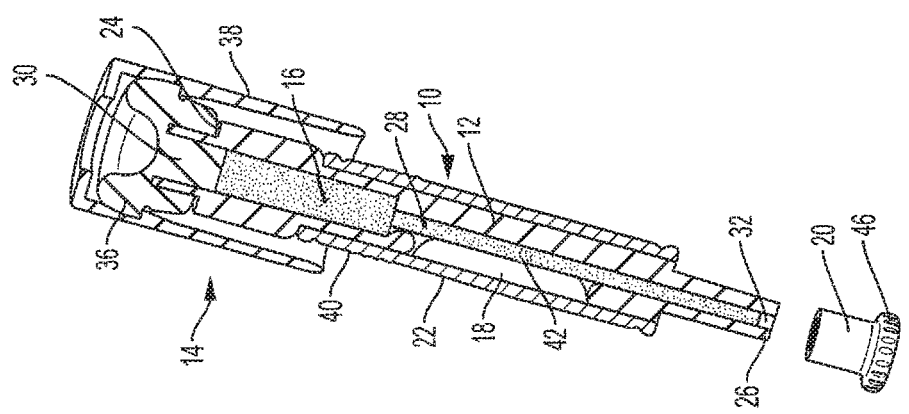
FIG. 5F is a partial cross-sectional perspective view of the activation member of the collection module of the biological fluid collection device of FIG. 1 being activated to dispense biological fluid from the collection module in accordance with an aspect of the present invention.

The blood sample is then dispensed from the collection module 10 by activation of the activation member 22, such as applying an inward pressure in the direction of the arrow on the portion of the elastic sleeve 40 covering the holding chamber 18 forcing the blood sample out of the holding chamber 18 and through the sample dispensing opening 32 (FIG. 5F). In this manner, the blood sample may be transferred to a device intended to analyze the sample, such as a point-of-care testing device, such as a cartridge tester or via a port while minimizing the exposure of the medical practitioner to the blood sample.

While a portion of the elastic sleeve 40 is shown and described as partially defining the holding chamber 18 and acting as the activation member 22 for dispensing the blood sample from the collection module 10, other alternative arrangements for achieving the same result are envisioned. For example, the holding chamber 18 may be wholly defined by the housing 12 and a separate activation device engaged with the holding chamber 18 may be activated to dispense the blood sample, including but not limited to, a plunger, push button, a slide, and the like.

Figure 4:
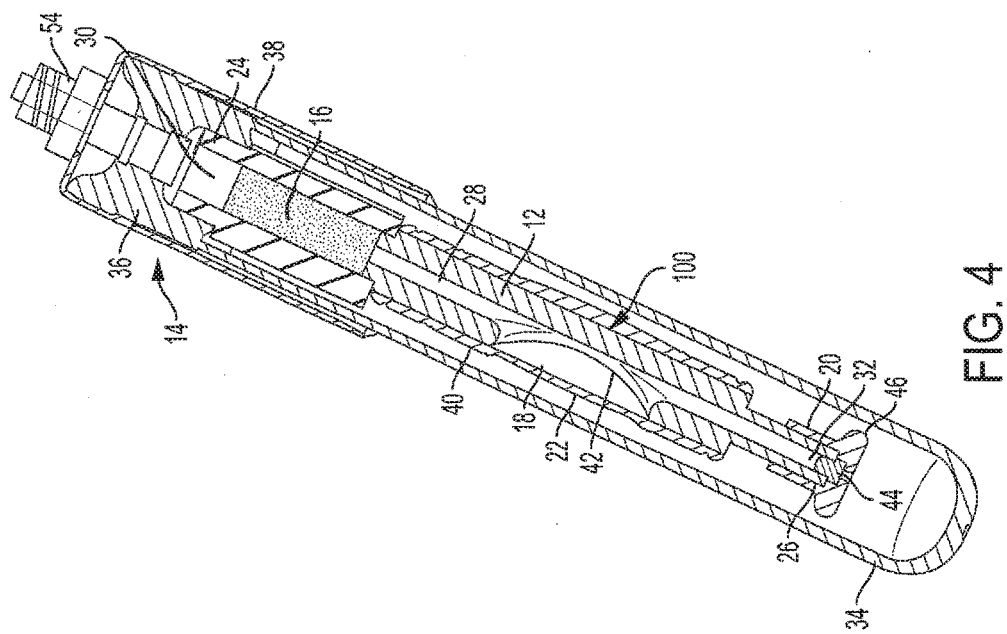
FIG. 4 is a partial cross-sectional perspective view of the biological fluid collection device of FIG. 3.
Figure 3:
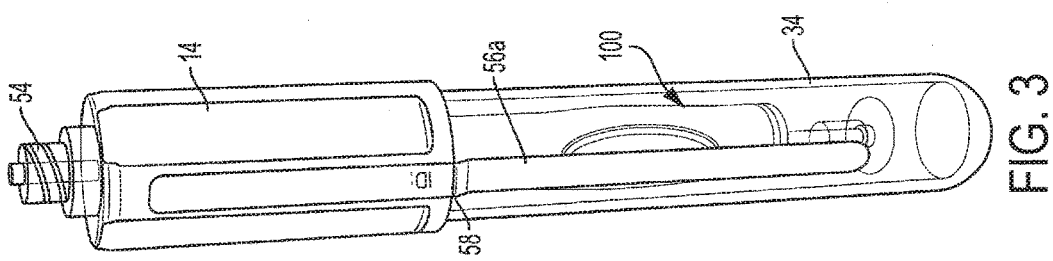
FIG. 3 is a front perspective view of a biological fluid collection device having a collection module disposed within an outer housing in accordance with another aspect of the present invention.

In another embodiment, shown in FIGS. 3 and 4, the closure 14 may have a luer lock connection 54 passing through the stopper 36. This configuration is useful when drawing a blood sample from an artery where no vacuum is necessary to pull the blood sample into the collection module 100 such as is necessary with venous blood collection. The collection module 100 is used in the same manner as the collection module 10 except that the luer lock connection 54 is used to connect the collection module 100 to a wing set or other collection means have a mating luer lock connection to introduce the blood sample into the passageway 28.

The collection modules 10, 100 may also be used without the outer housing 34. In the case of the collection module 10, a syringe or other power source may be used to draw the sample into the collection module 10. Further, while the discussion herein has focused on the use of the collection modules 10, 100 to collect a blood sample and mix it with an anticoagulant or other additive, the collection modules 10, 100 may also be used to collect any liquid sample, such as other bodily fluids, or may be used to provide mixing and dispensing of a sample that was already collected by another means.

Figure 8:
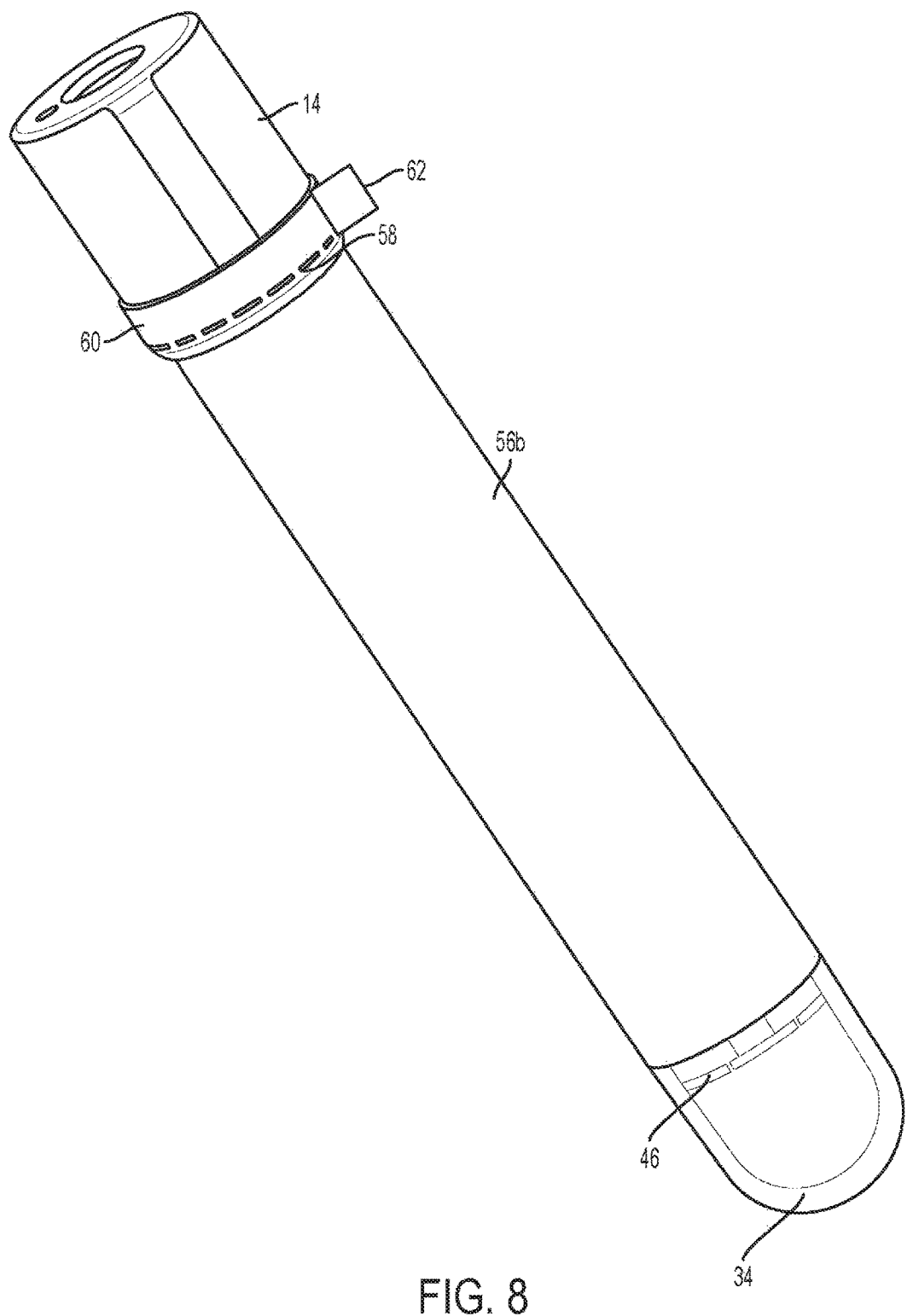
FIG. 8 is a perspective view of a biological fluid collection device in accordance with another aspect of the present invention.

In a further configuration, the collection module 10 may include a label 56*a*, 56*b* adhered to both the closure 14 and the outer housing 34 that must be broken to remove the collection module 10 from the outer housing 34. As shown in FIGS. 1-4, the label 56*a* may be a strip that only extends along a portion of the outer perimeter of the closure 14 and the outer housing 34. Twisting the closure 14 with respect to the outer housing 34 breaks the strip at the point where it transitions from the outer housing 34 to the closure 14. Perforations 58 may be provided in the label 56*a* at the point where it transitions from the outer housing 34 to the closure 14 to assist the strip in breaking when the closure 14 is twisted. Alternatively, as shown in FIG. 8, the label 56*b* may surround the entire perimeter of both the closure 14 and the outer housing 34. Perforations 58 are provided in the label 56*b* at the point where it transitions from the outer housing 34 to the closure 14 forming a band 60 around the closure 14 that may be separated from the portion of the label 56*b* surrounding the outer housing 34. Removal of the band 60 from the closure 14 allows the closure 14 to be removed from the outer housing 34. A pull tab 62 may be provided on the band 60 to assist in separating it from the portion of the label 56*b* surrounding the outer housing 34.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A biological fluid collection device comprising:
   a collection module comprising:
      a housing comprising:
         a first end having a sample introduction opening;
         a second end having a sample dispensing opening;
         a passageway extending between the sample introduction opening and the sample dispensing opening; and
         a holding chamber in fluid communication with the passageway;
      a closure covering the first end of the housing;
      a cap covering the second end of the housing and having a vented plug, the cap adapted to allow air to pass from the passageway of the collection module through the cap and the vented plug while preventing a blood sample from passing therethrough; and
      an activation member adapted to force a sample contained in the holding chamber out of the sample dispensing opening; and
   an outer housing having an open end and a closed end, wherein the collection module is positioned inside of the outer housing and the closure closes the open end of the outer housing.

2. The biological fluid collection device of claim 1, further comprising a mixing chamber in fluid communication with the passageway, wherein a sample introduced into the sample introduction opening passes through the mixing chamber and subsequently into the holding chamber.

3. The biological fluid collection device of claim 2, wherein the mixing chamber includes an anticoagulant adhered to an interior of the mixing chamber.

4. The biological fluid collection device of claim 2, wherein the mixing chamber is filled with an open cell foam.

5. The biological fluid collection device of claim 2, wherein the mixing chamber is positioned closer to the first end of the housing than the holding chamber such that a blood sample introduced into the sample introduction opening passes through the mixing chamber before passing into the holding chamber.

6. The biological fluid collection device of claim 1, wherein the holding chamber is defined by an elastic sleeve surrounding the housing and a recess in the housing.

7. The biological fluid collection device of claim 6, wherein the activation member is at least a portion of the elastic sleeve defining the holding chamber such that, when the cap is removed from the collection module, an inward pressure on the portion of the elastic sleeve defining the holding chamber toward the recess in the housing forces the blood sample in the holding chamber out of the sample dispensing opening.

8. The biological fluid collection device of claim 1, wherein the vented plug is a porous plug.

* * * * *